United States Patent [19]
Yamagishi et al.

[11] Patent Number: 6,048,913
[45] Date of Patent: Apr. 11, 2000

[54] COATING COMPOSITION FOR TEETH

[75] Inventors: Atsushi Yamagishi; Akira Oshima; Shigeto Kayane, all of Tokyo; Yukihiro Nakano, Wakayama, all of Japan

[73] Assignee: Kao Corporation, Tokyo, Japan

[21] Appl. No.: 09/125,420

[22] PCT Filed: Dec. 10, 1997

[86] PCT No.: PCT/JP97/04533

§ 371 Date: Aug. 17, 1998

§ 102(e) Date: Aug. 17, 1998

[87] PCT Pub. No.: WO98/26749

PCT Pub. Date: Jun. 25, 1998

[30] Foreign Application Priority Data

Dec. 19, 1996 [JP] Japan ...................................... 8-339653

[51] Int. Cl.[7] .............................. A61K 7/16; A61K 6/083
[52] U.S. Cl. .......................... 523/118; 524/547; 526/277; 260/998.17; 106/35
[58] Field of Search ............................ 523/118; 524/547; 526/277; 260/998.17

[56] References Cited

U.S. PATENT DOCUMENTS

| | | | |
|---|---|---|---|
| 4,274,933 | 6/1981 | Kamada et al. | 524/547 |
| 4,877,936 | 10/1989 | Engelbrecht | 523/118 |
| 5,079,277 | 1/1992 | Wilson et al. | 523/116 |
| 5,367,002 | 11/1994 | Huang et al. | 523/118 |
| 5,461,433 | 10/1995 | Nakabayashi et al. | 524/547 |
| 5,645,429 | 7/1997 | Blackwell et al. | 523/118 |

FOREIGN PATENT DOCUMENTS 2077943A 9/1992 Canada .

*Primary Examiner*—Andrew E. C. Merriam
*Attorney, Agent, or Firm*—Oblon, Spivak, McClelland, Maier & Neustadt, P.C.

[57] ABSTRACT

The present invention relates to a dental coating composition comprising a polymer which has in its molecule one or more phosphorus series acid residues selected from the group consisting of phosphoric acid, phosphonic acid and phosphinic acid and halides and salts thereof and has a weight-average molecular weight of 10,000 to 5,000,000, and water or a lower alcohol. The composition is a dental coating agent which does not easily peel off when drinking or eating, can be removed easily if necessary and does not have a safety problem.

11 Claims, No Drawings

COATING COMPOSITION FOR TEETH

TECHNICAL FIELD

The present invention relates to a dental coating composition, particularly a coating composition used for beautifying teeth.

BACKGROUND ART

Manicure and pedicure, as for cosmetic care of hands and fingernails and feet, are widely enjoyed by females. In recent years, cosmetic care of teeth has also become popular. This kind of dental care is generally carried out by applying a dye- or pigment-containing composition to teeth.

Use of a dental adhesive is one example of a technique for applying a composition to teeth. Specifically, a monomer or the like is applied to the teeth, followed by polymerization in a short time by ultraviolet irradiation or heating (ex. Japanese Patent Application Laid-Open No. SHO 53-69494 and Japanese Patent Application Laid-Open No. SHO 52-113089).

Considering the use, the above-described dental adhesive has a high adhesion strength such that it does not peel off from the teeth for a long period of time. For the purpose of dental beautification, on the other hand, the composition must have a proper adhesion strength such that it does not peel off easily during drinking or eating, but it can be removed easily if necessary. Since the above-described dental adhesive is polymerized in a short time using ultraviolet irradiation or the like, it impossible to control the adhesion strength or coating degree.

In addition, the above-described monomer involves a safety problem so it is often inappropriate to use the monomer for dental care at home.

An object of the present invention is therefore to provide a dental coating composition which does not peel off easily when drinking or eating, has a proper adhesion strength such that it can be removed easily if necessary and is highly safe in use.

DISCLOSURE OF THE INVENTION

In view of the forgoing circumstances, the present inventors have carried out an extensive investigation. As a result, it has been found that a dental coating composition comprising a polymer which has in its molecule a phosphorus series acid residue such as phosphoric acid and has a pre-determined weight-average molecular weight; and a specific solvent has an appropriate adhesion strength when applied to teeth, beautifies the teeth by imparting gloss or the like and is excellent in safety, leading to the completion of the invention.

In one aspect of the present invention, there is thus provided a dental coating composition comprising (a) a polymer which has in its molecule one or more phosphorus series acid residues selected from the group consisting of phosphoric acid, phosphonic acid and phosphinic acid, and halides and salts thereof and has a weight-average molecular weight of from 10,000 to 5,000,000; and (b) water or a $C_{1-5}$ alcohol.

In another aspect of the present invention, there is also provided a dental coating process, which comprises applying the above dental coating composition to teeth.

In a further aspect of the present invention, there is also provided the use of the above-described polymer (a) for the dental coating.

BEST MODES FOR CARRYING OUT THE INVENTION

The polymer (a) usable in the present invention has, in its molecule, one or more phosphorus series acid residues selected from the group consisting of phosphoric acid, phosphonic acid and phosphinic acid, and halides and salts thereof and has a weight-average molecular weight of 10,000 to 5,000,000.

Examples of the phosphoric acid residue contained in the polymer (a) include phosphate and diphosphate groups, each having at least one hydroxyl group, such as a phosphoric acid residue (1), phosphoric acid monoester residue (2), diphosphoric acid residue, (3) diphosphoric acid monoester residue (4) and diphosphoric acid diester residue (8) (each of the bonds in the below-described formulas (1) to (10) is bound to an atom other than oxygen, preferably, a carbon, nitrogen or sulfur atom, more preferably a carbon atom).

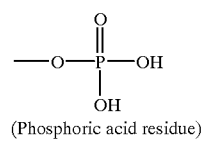
(Phosphoric acid residue) (1)

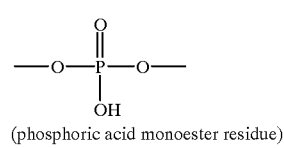
(phosphoric acid monoester residue) (2)

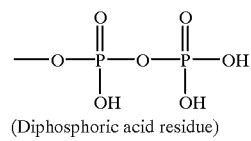
(Diphosphoric acid residue) (3)

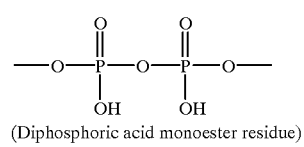
(Diphosphoric acid monoester residue) (4)

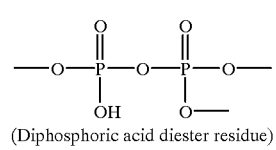
(Diphosphoric acid diester residue) (5)

Examples of the phosphonic acid residue include phosphonate or diphosphonate groups each having at least one hydroxyl group, such as a phosphonic acid residue (6), phosphonic acid monoester residue (7), diphosphonic acid residue (8) and diphosphonic acid monoester residue (9).

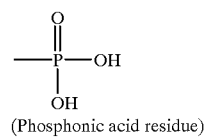
(Phosphonic acid residue) (6)

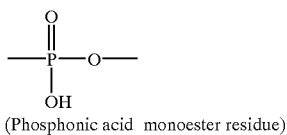
(Phosphonic acid monoester residue)

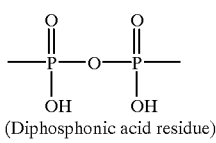
(Diphosphonic acid residue)

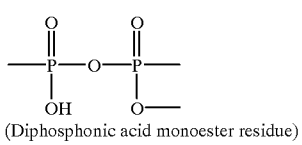
(Diphosphonic acid monoester residue)

Examples of the phosphinic acid residue include a phosphinic acid series residue (phosphinate group) (10).

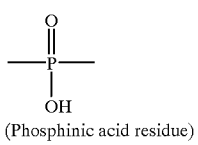
(Phosphinic acid residue)

As the salt of such a residue, preferred are alkali metal salts such as sodium and potassium salts.

Examples of the halide of such a residue include the groups of the above-described formulas (1) to (10) each of which has one or more hydroxyl groups substituted by a like number of chlorine atoms, bromine atoms, fluorine atoms or the like.

Among the groups of the above formulas (1) to (10), phosphoric acid residues [(1)–(5)] and salts thereof are more preferred from the viewpoints of appropriate adhesion strength and safety, with the phosphoric acid residue of the formula (1) and salt thereof are particularly preferred.

As the polymer (a), particularly preferred are those which have as a main chain a chain obtained by the polymerization of a polymerizable vinyl group and as a side chain the above-described phosphoric acid residue.

The polymer (a) may has as the side chain a group other than the above-described phosphoric acid residue. Described specifically, it may have as a side chain one or more of a carboxyl group and salts thereof, a sulfonic acid group and salts thereof, and saturated or unsaturated hydrocarbon groups which may be substituted by a hydroxyl group, amide group or fluorine.

The polymer (a) is preferred to have a phosphorus atom content of 0.0001 to 35 wt. %, particularly 0.1 to 10 wt. %. By incorporating the phosphorus series acid residue to give a phosphorus atom content in the polymer (a) to 0.0001 to 35 wt. %, a dental coating composition having more appropriate adhesion strength is available. Phosphorus atom contents less than 0.0001 wt. % do not bring about sufficient adhesion strength. When the content exceeds 35 wt. %, on the other hand, the composition happens to soften in the oral cavity.

As the polymer (a) used in the present invention, preferred is a homopolymer or copolymer having a structural unit represented by the following formula (11):

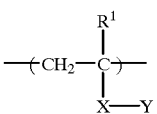

wherein $R^1$ represents a hydrogen atom or a hydrocarbon group which may be substituted by a fluorine atom, X represents an alkylene, $COOR^3$—, $CON(R^2)R^3$— or $COO[(CH_2)_mO]_nR^3$— group, in which $R^2$ representing a hydrogen atom or a $C_{1-5}$ hydrocarbon group, m standing for 1 to 10, n standing for 1 to 30, $R^3$ representing a divalent $C_{1-20}$ hydrocarbon group which may be substituted by a hydroxy, alkoxy or aryloxy group, and Y represents the above-described phosphorus series acid residue.

In the above formula (11), COOR— and $COO[(CH_2)_mO]_nR^3$— groups are preferred as X. Examples of the divalent hydrocarbon group represented by $R^3$ include linear or branched alkylene groups, divalent cycloalkyl groups and phenylene groups and combinations thereof.

The phosphorus series acid residue represented by Y in the above formula (11) may be esterified with a $C_{1-20}$ hydrocarbon group (ex. alkyl, phenyl or the like).

As the polymer (a), particularly preferred is a homopolymer or copolymer having a structural unit represented by the following formula (12):

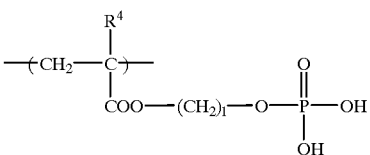

wherein $R^4$ represents a hydrogen atom or a methyl group and l stands for an integer of 1 to 15.

The weight-average molecular weight of the polymer (a) used in the present invention is 10,000 to 5,000,000, preferably 10,000 to 2,000,000, more preferably 15,000 to 1,000,000 and particularly preferably 20,000 to 1,000,000. When the weight-average molecular weight is less than 10,000, the strength of the formed film becomes low. When it exceeds 5,000,000, the polymer has poor solubility in a solvent and too high viscosity, which makes it difficult to treat the polymer.

Furthermore, the amount of the polymer (a) soluble in 100 g of anhydrous ethanol at 20° C. is preferably 1 g or greater, more preferably 5 g or greater and particularly preferably 10 g or greater. When the amount of the polymer soluble in 100 g of anhydrous ethanol at 20° C. is 1 g or greater, it becomes possible to prepare an easily applicable composition.

The polymer (a) can be obtained by polymerizing one or more monomers which contain the above-described phosphorus series acid residue or said monomer(s) and a monomer free from such a phosphorus series acid residue (said monomer will hereinafter be called "non-phosphorus series monomer").

The polymerization process differs depending on the monomer to be employed, but ordinary radical polymerization can be adopted.

Although no particular limitation is imposed on the above-described phosphorus-series-acid-residue-containing monomer insofar as it contains a polymerizable vinyl group as the main chain and the phosphorus series acid residue as the side chain, a monomer [CH$_2$=C(R$^1$)—X—Y] forming a structural unit of the above formula (11) is more preferred, with a (meth)acrylate having the phosphorus series acid residue as the side chain being particularly preferred.

As the above-described phosphorus-series-acid-residue-containing monomer, particularly preferred ones will be exemplified below:

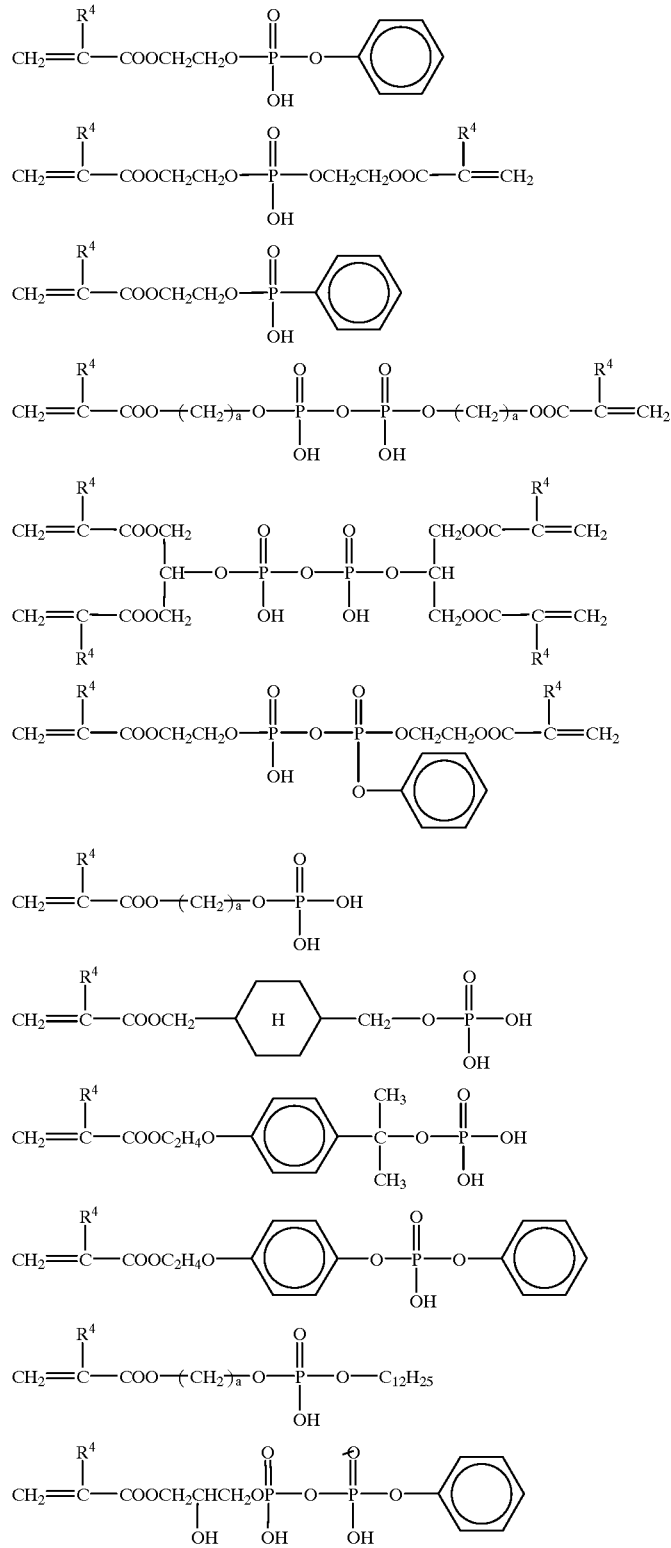

-continued
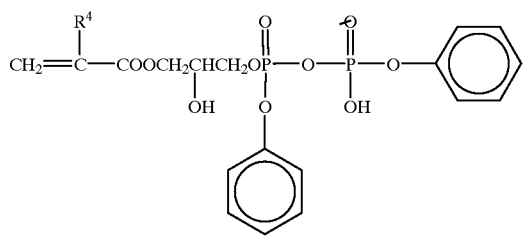
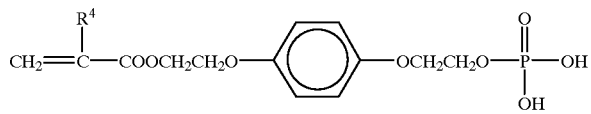
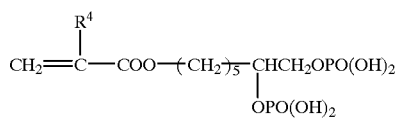
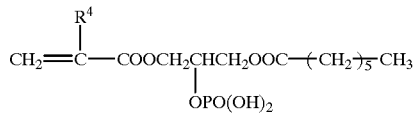
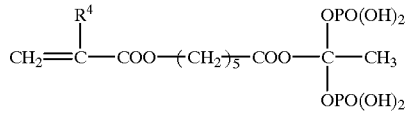
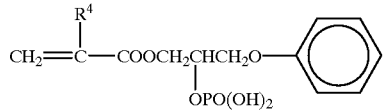
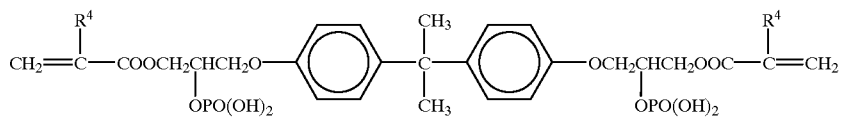
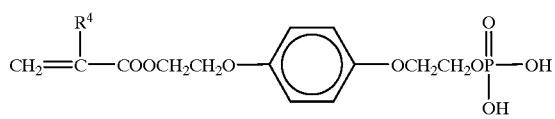
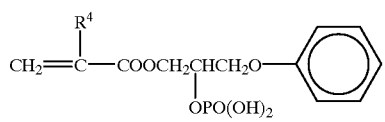
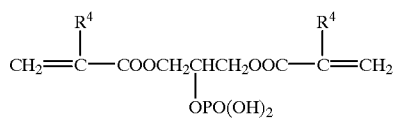
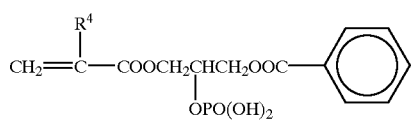
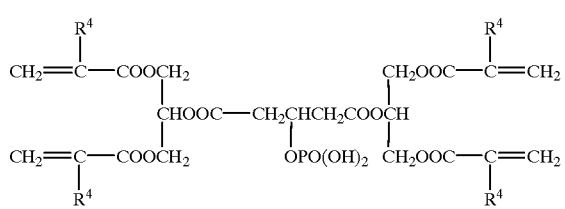

-continued

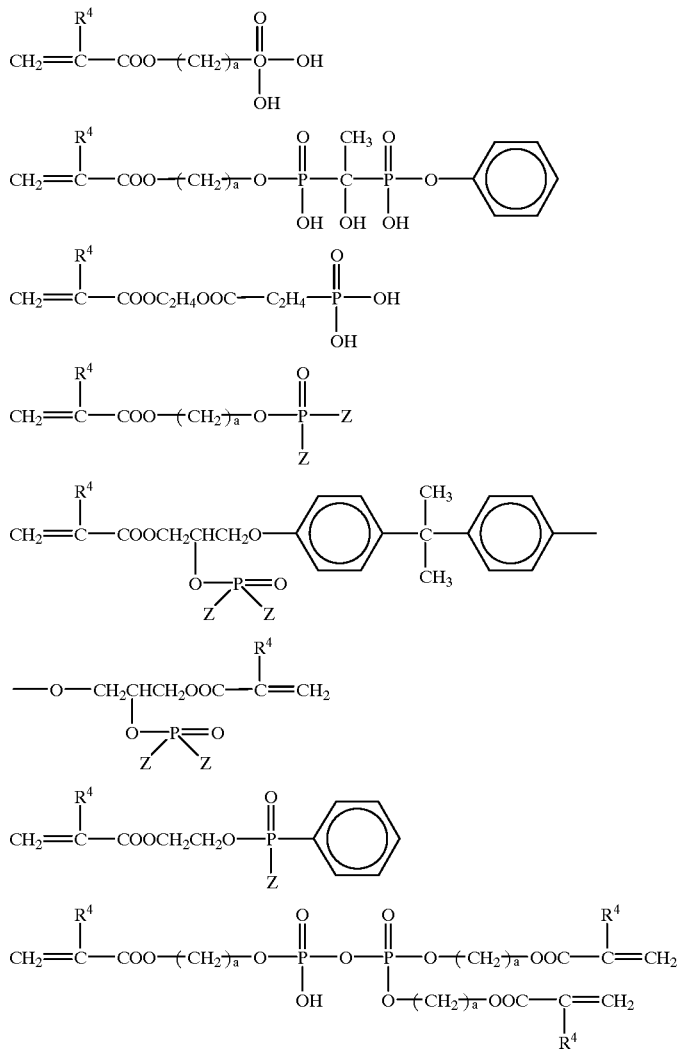

wherein $R^4$ represents a hydrogen atom or a methyl group, a stands for an integer of 2 to 40 and Z represents a halogen atom.

Among these monomers, those represented by the following formula (13):

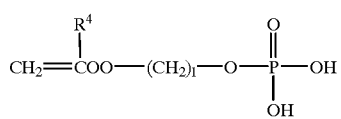
(13)

wherein $R^2$ represents a hydrogen atom or a methyl group and l stands for an integer of 1 to 15 are most preferred.

Examples of the non-phosphorus series monomer copolymerizable with any one of the above-exemplified phosphorus-series-acid-residue-containing monomers include (meth)acrylic acid, (meth)acrylate, (meth)acrylamide, vinyl carboxylate, styrene monomer, vinylpyridine, vinylpyrrolidone, maleimide monomer and unsaturated fatty acid monomer.

In addition, 2-methacryloyloxyethyltrimethylammonium chloride and 2-acryloyloxypropylhydrogen phthalate can also be given as examples.

Among the above-described non-phosphorus series monomers, preferably employed are one or more of (meth)acrylic acid, methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, 2-ethylhexyl (meth)acrylate, isobornyl (meth)acrylate, cetyl (meth)acrylate, lauryl (meth)acrylate, stearyl (meth)acrylate, dodecyl (meth)acrylate, dimethylaminoethyl (meth)acrylate, (meth)acrylic diethylene glycol ethoxylate, 2-methoxyethyl (meth)acrylate, 3-methoxybutyl (meth)acrylate, phenoxyethyl (meth)acrylate, tetrahydrofurfuryl (meth)acrylate, dimethylacrylamide, N-[3-(dimethylamino)propyl]acrylamide, diacetone acrylamide, cyclohexyl (meth)acrylate, vinyl acetate, vinyl propionate, vinyl butyrate, vinyl pivalate, vinyl caproate, vinyl octylate, vinyl caprylate, vinyl caprate, vinyl laurate, vinyl myristate, vinyl palmitate, vinyl stearate, vinyl neodecanoate, styrene, 2-methylstyrene, α-methylstyrene dimer, 2-vinylpyridine, 4-vinylpyridine, N-vinyl-2-pyrrolidone, N-phenylmaleimide, N-(2-chlorophenyl)maleimide, N-laurmaleimide and N-cyclohexylmaleimide.

Although no particular limitation is imposed on the mixing ratio of phosphorus-series-acid-residue-containing monomer to non-phosphorus series monomer in the copolymer used in the invention, the former monomer is preferably added in an amount of 0.01 to 40 mol %, particularly 0.1 to 20 mol %.

Water or a $C_{1-5}$ alcohol (b) to be incorporated in the composition of the present invention is a solvent having good affinity with the above-described polymer. Examples of the alcohol include linear or branched saturated alcohols having 1 to 5 carbon atoms. Among them, ethanol and isopropyl alcohol are preferred, with ethanol being particularly preferred. At least two of the solvents selected from water and $C_{1-5}$ alcohols may be used in combination. It is preferred that the solvent be added in an amount of 30 to 98 wt. %, particularly 50 to 95 wt. % in the whole composition.

The dental coating composition of the present invention is preferred to have a viscosity of 2 to 200 cp, particularly 5 to 50 cp when it is applied to teeth. If the viscosity is less than 2 cp, there is a possibility of the composition dripping in or outside the mouth. If the viscosity is greater than 200 cp, on the other hand, the composition does not spread well, which makes it difficult to apply the composition uniformly to the surface of the teeth. The viscosity of the composition as used herein is measured by a Brookfield type viscometer at 20° C.

To the dental coating composition of the present invention, a pigment can be added in order to make teeth look white, color the teeth or impart it with gloss. Examples of the pigment include titanium mica, fish scale leaves and shell powders. Among them, titanium mica is preferred because it imparts teeth with aesthetic appearance and gloss, flattens the coating unevenness and color can be changed by controlling the film thickness of the titanium on mica.

Such a pigment is preferred to be added in the powdery form so that it can be uniformly dispersed in the dental coating composition easily. The pigment is added to the coating composition preferably in an amount of 0.1 to 10 wt. %, more preferably 0.2 to 5 wt. %.

To the composition of the present invention, various powders can be added further as needed. Examples include α-quartz, silica, alumina, hydroxyapatite, calcium carbonate, fluoroaluminosilicate glass, barium sulfate, titanium oxide, zirconia, glass and ultra-fine-particle silica and organic complex powder containing both organic and inorganic components. Examples of the glass include, silica glass, sodium quartz silicate glass, borosilicate glass, barium glass, strontium glass, zinc glass, lanthanum glass, yttrium glass, barium boroaluminosilicate glass, alumina silicate glass, strontium boroaluminosiliate glass, synthetic silica and titanium silicate glass. To the composition of the present invention, a copolymer between polymethyl methacrylate or methyl methacrylate and a crosslinkable monomer, or a powdery polymer such as polystyrene or polyvinyl chloride is also added as needed.

To the dental coating composition of the present invention, orally usable various components can be added within an extent not impairing the advantages of the present invention. Examples of such components include tooth quality reinforcing agents such as sodium monofluorophosphate, tin fluoride and sodium fluoride; bactericides such as chlorhexidine and salts thereof, triclosan, cetylpyridinium chloride, isopropylmethylphenol, benzethonium chloride and benzalkonium chloride; pH regulators such as sodium phosphate, KOH and NaOH; enzyme preparations such as dextranase, amylase, protease, lysozyme and mutanase; anti-inflammatory agent blood circulation accelerator such as sodium chloride, hinokitiol, ε-aminocaproic acid, tranexamic acid, allantoin derivatives, tocopherol derivatives, octyl phthalide, nicotinic acid esters, dihydrocholesterol, glycyrrhetic acid, glycyrrhizic acid and salts thereof, glycerophosphate, chlorophyll, water-soluble inorganic phosphoric acid compounds, azulene derivatives, matricaria, Japanese green gentian, toki, cnidii rhizoma and other herbal and crude drugs; sweeteners such as saccharin sodium, stevioside, thaumatin and aspartylphenylalanine methyl ester; antiseptics such as p-hydroxybenzoic acid, ethyl p-hydroxybenzoate, propyl p-hydroxybenzoate, butyl p-hydroxybenzoate and sodium benzoate; colorants· coloring matters such as titanium dioxide; flavoring agents such as peppermint oil, spearmint oil, menthol, carvone, anethole, eugenol, methyl salicylate, limonene, ocimene, n-decyl alcohol, citronellol, α-terpineol, methyl acetate, citronellyl? acetate, methyl eugenol, ceneole, linalool, ethyl linalool, vanillin, thymol, anise oil, lemon oil, orange oil, sage oil, rosemary oil, cinnamon oil, pimento oil, laurel oil, beefsteak plant oil, methyl salicylate, clove oil and eucalyptus oil.

The dental coating composition of the present invention can be prepared, for example, by mixing the above-described polymer (a) and solvent (b) and, in addition, a thickener such as ethyl cellulose, hydroxypropylcellulose or carboxyvinyl polymer and a pigment such as titanium mica, fish scale leaves or shell powders as needed. It is necessary to select the thickener or pigment which is not harmful to the human body even when mistakenly ingested.

The dental coating composition of the present invention can be adhered to teeth by applying it to the teeth and then evaporating the solvent component from the composition. The composition adhered to the teeth can be removed easily by ethanol or the like.

EXAMPLES

The present invention will hereinafter be described more specifically by examples. It should however be borne in mind that the present invention is not limited to or by the following examples.

Example 1

In a 500-ml four-necked separable flask connected with a stirrer, condenser, dropping funnel and nitrogen inlet tube, 150 g of acetonitrile, 2.5 g of 2-methacryloyloxyethylacid phosphate and 47.5 g of ethyl methacrylate were charged, followed by bubbling with a nitrogen gas at a flow rate of 1.5 liters/min for 30 minutes, whereby the monomer solution was deaerated. After the deaerated monomer solution was heated to 60° C. with stirring in a hot water bath, a solution of 0.11 g of 2,2'-azobis(2,4-dimethylvaleronitrile) dissolved in 50 g of acetonitrile was added dropwise to the monomer solution from the dropping funnel over 30 minutes. The reaction mixture was then polymerized at 60° C. for 4 hours and 80° C. for 4 hours. Using 2 liters of a 1:1 methanol/water mixture as a reprecipitation solvent, reprecipitation was carried out twice for purification, whereby a phosphoric-acid-containing copolymer was obtained. The resulting copolymer had a weight-average molecular weight of 63,000 (in terms of polystyrene, the same applies hereinafter). The copolymer (20 g), 1 g of titanium oxide, 1 g of titanium mica and 78 g of ethanol were mixed, whereby Dental coating composition 1 was obtained.

Example 2

In a similar manner to Example 1 except that 2-methacryloyloxyethylacid phosphate was replaced by 6.5 g of the monomer represented by the following formula:

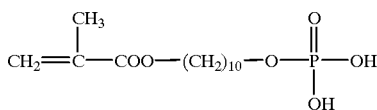

ethyl methacrylate was decreased to 41.9 g and 1.6 g of 2-hydroxyethyl methacrylate was added further, Dental coating composition 2 was obtained. Incidentally, the copolymer purified in this Example had a weight-average molecular weight of 105,000.

Example 3

In a similar manner to Example 1 except for the use of 12.3 g of the monomer represented by the following formula:

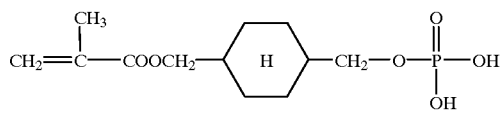

and 0.79 g of methacrylic acid instead of 2-methacryloyloxyethylacid phosphate and ethyl methacrylate, respectively, a phosphoric-acid-containing copolymer was obtained. The mixing of 30 g of the resulting copolymer, 2 g of titanium oxide, 0.5 g of titanium mica and 67.5 g of ethanol yielded Dental coating composition 3. Incidentally, the copolymer purified in this Example had a weight-average molecular weight of 52,000.

Example 4

In a similar manner to Example 1 except that 2-methacryloyloxyethylacid phosphate was replaced by 19.4 g of the monomer represented by the following formula:

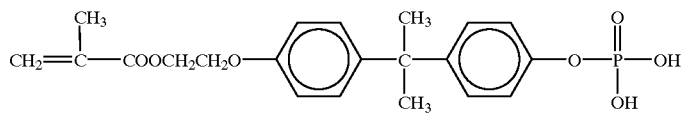

ethyl methacrylate was decreased to 28.7 g and 1.9 g of sodium styrenesulfonate was added further, a phosphoric-acid-containing copolymer was obtained. The copolymer had a weight-average molecular weight of 151,000. The mixing of 10 g of the resulting copolymer, 5 g of ethyl cellulose, 1 g of titanium oxide and 2 g of titanium mica, 1 g of powdery quartz, 0.1 g of a perfume and 80.0 g of ethanol yielded Dental coating composition 4.

Example 5

In a similar manner to Example 1 except that 2-methacryloyloxyethylacid phosphate was replaced by 7.2 g of the monomer represented by the following formula:

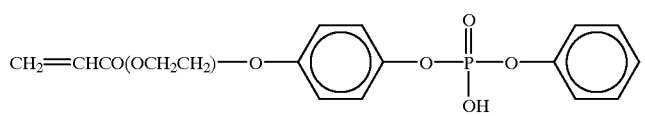

the amount of ethyl methacrylate was decreased from 47.5 g to 40.8 g and 1.2 g of dimethylacrylamide and 0.8 g of styrene were added further, a phosphoric-acid-containing copolymer was obtained. The resulting copolymer had a weight-average molecular weight of 77,000. The mixing of 15 of the copolymer, 2 g of ethyl cellulose, 1.5 g of titanium mica, 0.2 g of menthol, 0.2 g of sodium fluoride and 81.1 g of ethanol yielded Dental coating composition 5.

Example 6

In a similar manner to Example 1 except that 2-methacryloyloxyethylacid phosphate was replaced by 21 g of the monomer represented by the following formula:

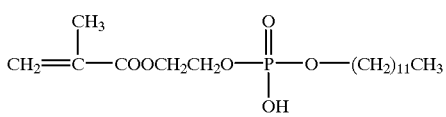

the amount of ethyl methacrylate was decreased from 47.5 g to 27.3 g and 1.0 g of N-vinyl-2-pyrrolidone and 0.6 g of vinyl acetate were added further, a phosphoric-acid-containing copolymer was obtained. The resulting copolymer had a weight-average molecular weight of 215,000. The mixing of 20 g of the copolymer, 0.5 g of titanium oxide, 5 g of powdery quartz, 0.2 g of sodium fluoride and 74.3 g of ethanol yielded Dental coating composition 6.

Example 7

In a similar manner to Example 1 except that 2-methacryloyloxyethylacid phosphate was replaced by 10 g of the monomer represented by the following formula:

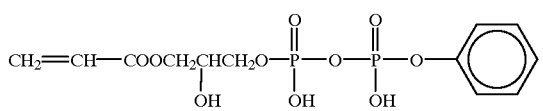

the amount of ethyl methacrylate was decreased from 47.5 g to 38.5 g, and 1.5 g of N-t-butylacrylamide was added further, Dental coating composition 7 was obtained. Incidentally, the copolymer purified in this Example had a weight-average molecular weight of 56,000.

Example 8

In a similar manner to Example 1 except that 2-methacryloyloxyethylacid prosphate was replaced by 18.7 g of the monomer represented by the following formular:

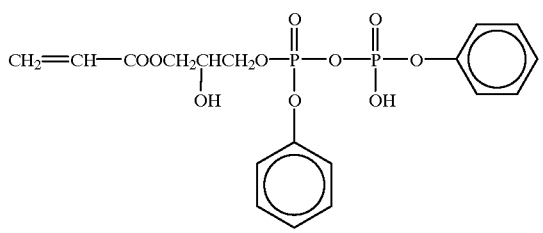

the amount of ethyl methacrylate was changed from 47.5 g to 29.7 g and 1.6 g of itaconic was added further, Dental coating composition 8 was obtained. The copolymer purified in this Example had a weight-average molecular weight of 116,000.

Example 9

In a similar manner to Example 1 except that 2-methacryloyloxyethylacid phosphate was replaced by 1.6 g of the monomer represented by the following formula:

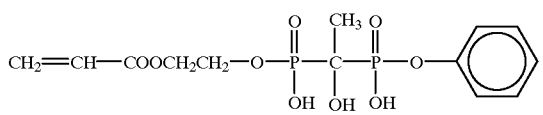

and the amount of ethyl methacrylate was increased from 47.5 g to 48.4 g, Dental coating composition 9 was obtained. Incidentally, the copolymer purified in this example had a weight-average molecular weight of 82,000.

Example 10

In a similar manner to Example 1 except that 2-methacryloyloxyethylacid phosphate was replaced by 5.1 g of the monomer represented by the following formula:

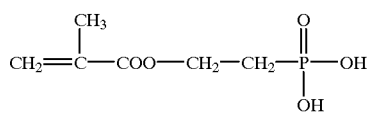

the amount of ethyl methacrylate was decreased from 47.5 g to 40.8 g, and 2.1 g of isopropyl acrylate and 2.0 g of dimethylacrylamide were added further, Dental coating composition 10 was obtained. Incidentally, the copolymer purified in this example had a weight-average molecular weight of 120,000.

Example 11

In a similar manner to Example 1 except that 2-methacryloyloxyethylacid phosphate was replaced by 3.3 g of the monomer represented by the following formula:

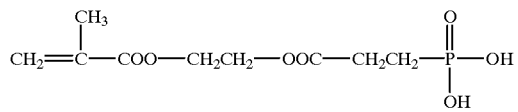

the amount of ethyl methacrylate was decreased from 47.5 g to 44.5 g and 1.3 g of 4-hydroxybutyl methacrylate and 1.0 g of vinylsulfonic acid were added further, Dental coating composition 11 was obtained. Incidentally, the copolymer purified in this example had a weight-average molecular weight of 104,000.

Example 12

In a similar manner to Example 1 except that 2-methacryloyloxyethylacid phosphate was replaced by 5.3 g of the monomer represented by the following formula:

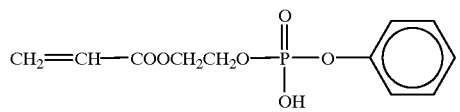

the amount of ethyl methacrylate was decreased from 47.5 g to 42.9 g and 1.8 g of methacrylic acid was added further, Dental coating composition 12 was obtained. Incidentally, the copolymer purified in this example had a weight-average molecular weight of 72,000.

Example 13

A mixed solution of 80 g of ethanol, 60.9 g of ethyl methacrylate, 19.1 g of 10-methacryloyloxydecylacid phosphate (similar to the substance used in Example 2) and 0.15 g of V-65 (azo series polymerization.initiator) was bubbled with a nitrogen gas for 30 minutes, whereby the monomer solution was deaerated. In a 500-ml four-necked separable flask equipped with a stirrer, condenser, dropping funnel and nitrogen inlet tube, a 20 wt. % portion of the monomer solution was charged and polymerized at 62° C. for 10 minutes under a nitrogen atmosphere. The remaining portion of the monomer solution was added dropwise to a polymerization tank over 2 hours. After the completion of the dropwise addition, polymerization was continued for further 6 hours at 62° C. After polymerization, purification was effected twice by using 3 liters of a 1:2 (volumetric ratio) methanol/water as a reprecipitation solvent. The polymer so obtained had a molecular weight of 960,000.

Comparative Example 1

Comparative product 1 was obtained by mixing 30 parts by weight of shellac (an extract of the insect coccidium, Gifu Shellac Co., Ltd.), 68 parts by weight of ethanol, 1 part by weight of titanium oxide and 1 part by weight of titanium mica.

Comparative Example 2

HANIC (produced by HANICS Corp.) was used.

Test 1

Test on peeling caused by eating or drinking was performed. Twenty eight panelists were divided into four groups, each 7 panelists. Dental coating composition 1 was applied to the whole surface of each of the six anterior teeth of the upper jaw of the first group at 9 a.m. and the picture of the anterior teeth was taken. Similarly, Dental coating composition 2, Comparative product 1 and Comparative product 2 were applied to the second group, third group and fourth group, respectively, followed by photographing. Each panelist took 200 ml of water at 10 a.m., one commercially-available hamburger, one commercially-available fried chicken, 100 g of a lettuce and tomato salad, one boiled potato and 200 ml of commercially available oolong tea at 0 p.m., and 200 ml of water at 3 p.m. At 6 p.m., the picture of the anterior teeth was taken, which was compared with the picture taken at 9 a.m., whereby the remaining degree of the dental coating composition or comparative product on the teeth was judged in accordance with the following standards. Results are shown in Table 1.

Evaluation standards:

3 scores: No peeling was observed.

2 scores: Peeling was observed only at the tip point of the teeth.

1 score: Peeling occurred on less than the one-fourth of the coated surface.

0 score: Peeling occurred on not less than the one-fourth of the coated surface.

TABLE 1

|  | Average scores by seven panelists |
| --- | --- |
| Dental coating composition 1 | 2.13 |
| Dental coating composition 2 | 2.20 |
| Dental coating composition 13 | 2.30 |
| Comparative product 1 | 0.51 |
| Comparative product 2 | 0.47 |

It has been understood from Table 1 that each of the dental coating compositions according to the present invention does not easily cause peeling even by drinking or eating.

Test 2

Subsequent to phosphoric acid etching, "Panavia EX" (produced by Kuraray Co., Ltd.), a dental adhesive, was applied to bovine teeth in a manner known per se in the art. Similarly, the compositions of Examples 1, 2 and 3 were applied to the bovine teeth, respectively. After immersion in an artificial saliva ("Salivate", produced by Teijin Limited) at 36° C. for 24 hours, the teeth so treated were subjected to a removal test by using absorbent cotton soaked with ethanol. The dental adhesive was not removed completely by ethanol, while Dental coating compositions 1, 2 and 3 according to the present invention were almost completely removed.

CAPABILITY OF EXPLOITATION IN INDUSTRY

The present invention has made it possible to provide a dental coating composition which does not easily peel off when eating or drinking; has a proper adhesion strength such that it can be easily removed if necessary; and does not have a safety problem. In addition to the beautifying effects, the composition is expected to have effects for preventing tooth decay, hyperesthesia or tartar by forming a strong film on the surface of the teeth. Furthermore, it is possible to expect that the dental coating composition of the present invention will contribute to prevention of gingivitis diseases because of its effective suppressibility against bacterial plaque.

We claim:

1. A dental coating composition, comprising (a) a polymer of polymerized vinyl monomers which has in a molecule thereof one or more phosphorus series acid residues selected from the group consisting of phosphoric acid, phosphonic acid and phosphinic acid, and halides and salts thereof and has a weight-average molecular weight of 10,000 to 5,000,000; and (b) a saturated $C_{1-5}$ alcohol or a mixture of water and a saturated $C_{1-5}$ alcohol, wherein the amount of said polymer (a) soluble in 100 g of anhydrous ethanol at 20° C. is at least 1 g, and wherein said polymer (a) is a homopolymer or copolymer having a structural unit represented by the following formula (11):

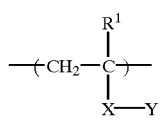
(11)

wherein $R^1$ represents a hydrogen atom or a hydrocarbon group which may be substituted by a fluorine atom, X represents an alkylene, $COOR^1$—, $CON(R)R^1$— or $COO((CH_2)_mO)_nR^3$— group, in which $R^2$ represents a hydrogen atom or a $C_{1-5}$ hydrocarbon group, m is 1 to 10, n is 1 to 30 and $R^3$ represents a $C_{1-20}$ divalent hydrocarbon group which may be substituted by a hydroxy, alkoxy or aryloxy group, and Y represents a phosphorus series acid residue selected from the group consisting of phosphoric acid, phosphonic acid and phosphinic acid.

2. A composition according to claim 1, wherein said polymer (a) is a polymer having a residue of phosphoric acid or a salt thereof.

3. A composition according to claim 1, wherein said polymer (a) has, as a main chain, a chain obtained by polymerization of a polymerizable vinyl group and, as a side chain, one or more phosphorus series acid residues selected from the group consisting of phosphoric acid, phosphonic acid and phosphinic acid, and halides and salts thereof.

4. A composition according to claim 1, wherein the phosphorus atom content in said polymer (a) is 0.0001 to 35 wt. %.

5. A composition according to claim 1, which has a viscosity of 2 to 200 cp.

6. A composition according to claim 1, wherein said polymer (a) is a copolymer of a polymerizable monomer containing in a molecule thereof one or more phosphorus series acid residues selected from the group consisting of phosphoric acid, phosphonic acid and phosphinic acid, and halides and salts thereof; and a polymerizable monomer free from said phosphorus series acid residue.

7. A composition according to claim 1, wherein said polymer (a) is a homopolymer or copolymer having a structural unit represented by the following formula (12):

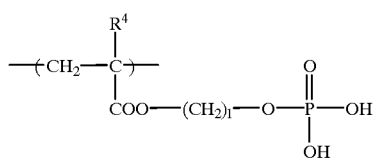

(12)

wherein $R^4$ represents a hydrogen atom or a methyl group and l stands for an integer of 1 to 15.

8. A composition according to claim 1, further comprising a pigment selected from the group consisting of titanium on mica, fish scale leaves and shell powders.

9. A composition according to claim 8, wherein the pigment content is 0.01 to 10 wt. %.

10. A dental coating method, which comprises applying a composition as claimed in claim 1 to a tooth.

11. A composition according to claim 1, consisting essentially of defined components (a) and (b).

* * * * *

UNITED STATES PATENT AND TRADEMARK OFFICE
CERTIFICATE OF CORRECTION

PATENT NO. : 6,048,913

DATED : April 11, 2000

INVENTOR(S) : Atsushi YAMAGISHI et al.

It is certified that error appears in the above-identified patent and that said Letters Patent is hereby corrected as shown below:

Column 20, line 2, "titanium on" should read --titanium--.

Signed and Sealed this

Third Day of April, 2001

*Attest:*

NICHOLAS P. GODICI

*Attesting Officer*     Acting Director of the United States Patent and Trademark Office